United States Patent [19]

Maak et al.

[11] Patent Number: 4,784,667
[45] Date of Patent: Nov. 15, 1988

[54] OXIDATION HAIR DYES COMPRISING DIAMINO-SUBSTITUTED PYRIDINES AND AMINO-SUBSTITUTED AROMATICS AS PRECURSORS

[75] Inventors: Norbert Maak, Neuss; Peter Flemming, Oberhausen; Dieter Schrader, Duesseldorf, all of Fed. Rep. of Germany

[73] Assignee: Henkel Kommanditgesellschaft auf Aktien, Duesseldorf, Fed. Rep. of Germany

[21] Appl. No.: 786,135

[22] Filed: Oct. 7, 1985

Related U.S. Application Data

[63] Continuation-in-part of Ser. No. 521,747, Aug. 19, 1983, abandoned.

[30] Foreign Application Priority Data

Sep. 10, 1982 [DE] Fed. Rep. of Germany ....... 3233540

[51] Int. Cl.$^4$ ................................................ A61K 7/13
[52] U.S. Cl. ............................................................ 8/409
[58] Field of Search ............................................. 8/409

[56] References Cited

U.S. PATENT DOCUMENTS 4,473,375 9/1984 Clausen .................................. 8/409

FOREIGN PATENT DOCUMENTS 1142045 1/1963 Fed. Rep. of Germany .
1492158 1/1970 Fed. Rep. of Germany .
1617831 4/1972 Fed. Rep. of Germany .

Primary Examiner—Albert T. Meyers
Assistant Examiner—John M. Kilcoyne
Attorney, Agent, or Firm—Ernest G. Szoke; Henry E. Millson, Jr.; Wayne C. Jaeschke

[57] ABSTRACT

This invention is directed to oxidation hair dye compositions and their use in the dyeing of human hair. The compositions consist essentially of precursors comprising 2,3-diamino-6-methoxy-pyridines and aromatic amines or diamines. The combination of oxidation dye precursors according to the invention gives bright, deep blue dye finishes having high stability to heat and light.

8 Claims, No Drawings

OXIDATION HAIR DYES COMPRISING DIAMINO-SUBSTITUTED PYRIDINES AND AMINO-SUBSTITUTED AROMATICS AS PRECURSORS

This is a continuation-in-part of Ser. No. 521,747, filed Aug. 19, 1983 and now abandoned.

FIELD OF THE INVENTION

This invention is directed to oxidation hair dyes. More specifically, this invention is directed to the use of diamino-substituted pyridines and amino-substituted aromatics as precursors in oxidation hair dyes.

BACKGROUND OF THE INVENTION

Dyes known as oxidation dyes, which are produced by oxidative coupling of one or more developer components with one or more coupling components, are preferred due to their intense colors, the mild reaction conditions under which they are formed, and their very good fastness properties. Nitrogen bases such as primary aromatic amines with an additional hydroxyl or unsubstituted or substituted amino group in ortho- or para-position, diamino-pyridine derivatives, 4-aminopyrazolone derivatives, heterocyclic hydrazone derivatives, and tetraaminopyrimidines are generally used as developer substances. Phenols, m-phenylene diamine derivatives, naphthols, certain resorcinol derivatives, and pyrazolones are known to be useful as coupling components.

Good oxidation dyestuff components must meet the following requirements: They must produce the desired color nuances in sufficient intensity during oxidative coupling with the respective developer or coupling component. Also, they must possess a capacity for being absorbed by human hair without excessive coloring of the scalp. In addition, they should be toxicologically and dermatologically safe.

The production of the strongest possible color shades closely corresponding to the natural hair color nuances is also important. Furthermore, the general stability of the dyestuffs produced as well as their fastness to light and to washing and their thermostability, have very special significance for the prevention of color shifts from the original color nuance or even a change in color to different shades. In addition, in the hair dyeing field there is always an interest in new oxidation dye components that can be combined with the known dye components to produce new color nuances of cosmetic value.

The use of diaminopyridines as oxidation dye precursors is known from German Offenlegungsschrift (DE-OS) No. 11 42 045. German Offenlegungsschrift (DE-OS) No. 14 92 158 describes other amino- and oxy-pyridines for the production of oxidation dyes. However, the oxidation dyes obtained from the pyridine derivatives described in those publications are unsatisfactory with regard to both depth of color and fastness.

German Offenlegungsschrift (DE-OS) No. 16 17 831 describes a process for dyeing human hair using pyridine dye precursors, in which a quantity of reducing agent exceeding the concentration normally used to prevent the premature oxidation of dye precursors is added to obtain greater depth of color. This process has the disadvantage that benzoic dye precursors, for example, couplers, cannot be used for modifying the colors because they are excessively weakened by the reducing agent used.

Accordingly, the search for better oxidation hair dyes includes the task of finding and combining with one another suitable oxidation dye precursors which give both strong and deep colors and which also show high stability to heat and light. In addition, suitable oxidation dye precursors must demonstrate favorable toxicological and dermatological properties.

OBJECTS OF THE INVENTION

It is an object of the invention to provide agents for the oxidative dyeing of hair that are based upon diamino-substituted pyridines and amino-substituted aromatics.

It is also an object of the invention to provide a process for dyeing hair wherein a novel hair dyestuff is employed.

It is a further object of the invention to provide an oxidative hair dyestuff composition comprising (1) at least one 2,3-diamino-6-methoxy-pyridine of the formula

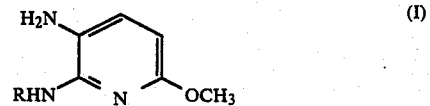

wherein R is methyl or hydroxyethyl, in combination with (2) at least one compound selected from the group consisting of aromatic diamines, 2-aminophenol, and 4-aminophenol, as oxidation dye precursors.

These and other objects of the invention will become more apparent in the discussion below.

DETAILED DESCRIPTION OF THE INVENTION

Applicants have found novel hair dyestuffs that satisfy the above-mentioned requirements. The hair dyestuffs are based upon oxidation hair dyes comprising (1) at least one 2,3-diamino-6-methoxy-pyridine of the formula

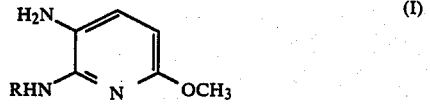

wherein R is methyl or hydroxyethyl, in combination with (2) at least one compound selected form the group consisting of aromatic diamines, 2-aminophenol, and 4-aminophenol, as oxidation dye precursors.

The compounds of Formula I may be combined in hair dyes according to the invention with, for example, o-phenylene diamine, p-phenylene diamine, 2-aminophenol, 4-aminophenol, and/or derivatives of these compounds which contain one or two $C_1$-$C_4$ alkyl substituents or $C_2$-$C_4$ hydroxyalkyl substituents on the nitrogen atom and/or one or more $C_1$-$C_4$-alkyl substituents and/or alkoxy substituents having from 1 to 4 carbon atoms in the alkyl moiety and/or halogen atoms on the aromatic nucleus. Examples of substituted aromatic diamines include, for example, 2,3-diaminotoluene, 2,5-diaminotoluene, 2,3-diaminoanisole, 2,5-diaminoanisole, N-methyl-p-phenylene diamine, N,N-dimethyl-p-phenylene diamine, N,N-diethyl-2-methyl-p-phenylene diamine, N-ethyl-N-(2-hydroxyethyl)-p-phenylene diamine, chloro-p-phenylene diamine, N,N-bis-(2-hydroxyethyl)-p-phenylene diamine, 2-chloro-6-bromo-p-phenylene diamine, 2-chloro-6-methyl-p-phenylene diamine, 6-methoxy-3-methyl-p-phenylene diamine, and N-(2-hydroxypropyl)-p-phenylene diamine.

Depth of color and fastness are particularly pronounced when the compounds corresponding to Formula I are combined with p-phenylene diamine, p-tolylene diamine, and/or 2,5-diaminoanisole in the hair dyes.

The compounds corresponding to Formula I are standard, commercially available products.

In addition to the characteristic oxidation dye precursors mentioned above, the hair dyes according to the invention may contain other conventional developer substances, coupler substances, and/or directly attaching dyes. Conventional developer components include, for example, heterocyclic hydrazone derivatives, 4-amino-pyrazolone derivatives, tetraaminopyrimidines, and other known aminopyridines. Suitable conventional coupler substances include, for example, m-phenylene diamine derivatives, m-aminophenols, phenols, resorcinol derivatives, naphthols, and pyrazolones. Nitrophenylene diamine derivatives are examples of suitable, conventional directly attaching dyes.

The hair dyes according to the invention where R is a methyl or a hydroxyethyl are distinguished by the fact that extremely bright dye finishes having high stability to heat and light are obtained. In addition, these hair dyes according to the invention where R is a methyl or a hydroxyethyl, when applied to hair, are distinguished by exceptional fastness to cold permanent waving, to friction and to perspiration. There is no need for large additions of reducing agents to the hair dyes.

In the hair dyestuffs according to the invention, the compounds of Formula I (1) and the aromatic diamines or amines (2) generally are used in approximately equimolar quantities. In instances where other conventional developer substances and/or coupler substances are used, it is best to employ the coupler substances in substantially molar quantities, based upon the developer substances used. However, although it is best to use molar quantities, there is no disadvantage in using a certain excess or deficiency of individual oxidation dye precursors. For example, oxidation dye precursors and/or coupling and developer components can be present in a molar range of from about 2:1 to 1:2, a 10% or less excess or deficiency being preferred.

In addition, it is not necessary that the compounds of Formula I and aromatic amines or diamines, or any conventional couplers, developers, or directly attaching dyes, are homogeneous or pure products. On the contrary, the compounds of Formula I, the aromatic amines or diamines, the conventional couplers, the conventional developers, and the conventional directly attaching dyes may each consist of mixtures thereof according to the invention.

The oxidative coupling, that is, the development of the dye, can in principle be carried out with atmospheric oxygen, as is done with other oxidation hair dyestuffs also. However, chemical oxidation agents are advantageously employed, especially when the hair is to be lightened as well as dyed. Particularly suitable as such oxidation agents are hydrogen peroxide or its adducts with urea, melamine, or sodium borate as well as mixtures of such hydrogen peroxide adducts with potassium peroxydisulfate.

For the preparation of the hair dyes according to the invention, the oxidation dye intermediate products are incorporated into suitable cosmetic preparations such as, for example, creams, emulsions, gels, foam aerosols, foaming solutions containing tensides, such as shampoos, or other products suitable for application to the hair. Conventional components of such cosmetic preparations include, for example, wetting and emulsifying agents such as anionic, nonionic, or ampholytic tensides, for example, sulfates of fatty alcohols, alkane sulfonates, α-olefin sulfonates, polyglycol ether sulfates of fatty alcohols, adducts of ethylene oxide onto fatty alcohols, fatty acids, or alkyl phenols, sorbitan fatty acid esters, partial glycerides of fatty acids, and alkanolamides of fatty acids; thickeners such as methyl or hydroxyethyl cellulose, starch, fatty alcohols, liquid paraffin, or fatty acids; perfume oils; and hair-conditioning and grooming additives such as water-soluble cationic polymers, protein derivatives, pantothenic acid, or cholesterol.

The above-mentioned additives are added in the amounts normal for these purposes. For example, wetting and emulsifying agents can be present in concentrations of from about 0.5 to 30 percent by weight, preferably from about 1 to 15 percent by weight, and thickeners can be present in concentrations of from about 0.1 to 25 percent by weight, preferably from about 1 to 15 percent by weight, based, respectively, upon the total weight of the hair dye preparation. The concentration of the oxidation dye precursors in the hair dye preparations is from about 0.2 to 5 percent by weight, preferably from about 1 to 3 percent by weight, based upon the weight of the total weight of the hair dye preparation.

A hair dye according to the invention can be applied in a mildly acidic, neutral, or alkaline medium, regardless of the form of the cosmetic preparation, for example, a cream, gel, or shampoo. The cosmetic preparation is preferably used in a pH range of from about 8 to 10 and is applied at a temperature range of from about 15° to 40° C., especially preferably at room temperature. After the hair dye is allowed to react for a sufficient time, usually approximately 30 minutes, the preparation is removed by rinsing from the hair to be dyed. The hair is then washed with a mild shampoo and dried. Shampooing would be unnecessary if the hair dye preparation itself, for example, a coloring shampoo, has a high tenside content. The hair, which can be any color or length, can be eiher "live" human hair or human hair that has been cut, such as that in a wig.

The colors that can be achieved with the hair dyes according to the invention where R is a methyl or a hydroxyethyl are characterized by brightness and by superior resistance, that is, fastness, to heat, light, washing, rubbing, as well as fastness to cold permanent waving, to friction, and to perspiration.

The following examples are intended to illustrate the invention and are not to be construed as limiting the invention thereto.

EXAMPLES

The hair dyes according to the invention were comparatively tested against hair dyes containing other aminopyridines (instead of 2,3-diamino-6-methoxy-pyridine) in a hair dye cream emulsion having the following composition:

| Component | Amount |
|---|---|
| $C_{12}$-$C_{18}$-fatty alcohol | 10 gm |
| $C_{12}$-$C_{14}$-fatty alcohols + 2 EO sulfate, Na-salt (28%) | 25 gm |
| Water | 60 gm |
| Aminopyridine | 0.005 mol |
| Aromatic amine or diamine | 0.005 mol |
| Conc. ammonia solution | up to pH = 9.5 |
| Water | q.s. ad 100 gm |

The components were mixed with one another in the order indicated above. After addition of the oxidation dye precursors, the pH value of the emulsion was first adjusted to 9.5 with concentrated ammonia solution, followed by addition of water to a total of 100 gm.

Oxidative development of the dye was carried out with 1% hydrogen peroxide solution as oxidizing agent. Ten grams of hydrogen peroxide solution (1%) were added to and mixed with 100 gm of the emulsion.

The dye cream was applied to approximately 5-cm long strands of standardized human hair (90% gray, but not specially pre-treated) and left for 30 minutes at 35° C. After dyeing, the hair was rinsed, washed with a normal shampoo, and then dried.

The following compounds were used as the aminopyridines:

A-1 = 3-amino-2-methylamino-6-methoxypyridine (according to the invention)
A-2 = 3-amino-2-(2-hydroxyethyl)-amino-6-methoxy pyridine (according to the invention)
V-4 = 2,3-diamino-6-methyoxypyridine (comparison)
V-1 = 2-dimethylamino-3,5-diaminopyridine (comparison)
V-2 = 2,6-diaminopyridine (comparison)
V-3 = 2,5'-diamino-bis-(2-pyridyl)-amine (comparison)

The compounds A-1, A-2, and A-3, are conventional commercial products which were obtained from Chemische Fabrik Weyl, Mannheim.

The following compounds were used as aromatic diamines:
PPD = p-phenylene diamine
PTD = p-tolylene diamine The dye finishes obtained with these oxidation dye precursors are shown in the following table:

TABLE I

| Example No. | Aminopyridine | Aromatic Diamine | Color Obtained |
|---|---|---|---|
| 1 | A-1 | PPD | blue-black |
| 2 | A-2 | PPD | blue-black |
| 3 | V-4 | PPD | blue-black |
| 4 | A-1 | PTD | blue-black |
| 5 | A-2 | PTD | blue-black |
| 6 | V-4 | PTD | blue-black |
| 7 | V-1 | PPD | blue |
| 8 | V-2 | PPD | blue |
| 9 | V-3 | PPD | brown |
| 10 | V-1 | PTD | blue-gray |
| 11 | V-2 | PTD | blue |
| 12 | V-3 | PTD | brown |

The hair dyes of Examples 4 and 5 according to the invention and the comparison hair dyes of Examples 6, 10, 11, and 12 were tested for stability to heat and light. In addition the hair dyes of A-1 and A-2 with PTD according to the invention and the comparison hair dye of V-4 with PTD were tested for fastness to cold permanent waving, to friction, and to perspiration.

Heat stability test:

The dyed strands of hair were stored for seven days at 45° C. in a thermostatically controlled drying cabinet. Thereafter, the color was compared with that of a sample of the same dye finish stored at 20° C.

Light stability test:

The light stability of the dyed strands of hair was determined in accordance with DIN 54004 (April, 1966), Section 7.5.2. The method of testing essentially comprises exposing the dyed strands of hair together with textile specimens of eight blue, stability-graduated reference colorings of the light stability scale, to the light of a xenon arc lamp with a color temperature of 5500° to 6500° K. The strands and textile specimens are fastened alongside one another to a card, and the peripheral zones of the strands and the textile specimens are masked parallel to the longitudinal edge of the card. Exposure is continued with frequent inspections by removal of the mask until reference coloring 3 on the light stability scale shows a difference which can just be noticed between the exposed part and the unexposed part. The samples are then inspected for changes which are optionally evaluated by comparison with the changes in reference colorings 1, 2, and 3 of the light stability scale. Exposure is then continued until reference coloring 4 of the light stability scale again shows a difference in color which can just be noticed between the now exposed part and the unexposed part. The masking plate is then replaced by a larger masking plate which covers approximately one-third of the previously exposed surface parallel to the longitudinal edge. Exposure is continued until reference coloring 6 of the light stability scale shows a difference in color which can just be noticed. Light stability is determined by comparing the contrasts on the strands of hair with the contrasts on the reference colorings of the light stability scale.

The results of the heat stability and light stability tests are shown in the following table:

TABLE II

| Example No. | Light Stability Rating | Heat Stability |
|---|---|---|
| 4 | 4–5 | stable, unchanged |
| 5 | 3–4 | stable, unchanged |
| 6 | 3–4 | stable, unchanged |
| 10* | 3 | unstable, brown |
| 11* | 3 | unstable, much darker |
| 12* | 3 | unstable, much darker |

*Comparison

COMPARISON TESTS

The comparison testing of coupling agents of Formula (I)

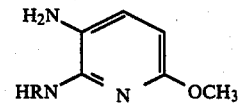

in which
R = $CH_3$ (A 1)
R = $CH_2$—$CH_2$—OH (A 2)
compared to R = H (V 4), 2,3-diamino-6-methoxypyridine according to U.S. Pat. No. 3,200,040.

Creme hair dyes of the following composition were produced:

| | |
|---|---|
| $C_{12}$-$C_{18}$ fatty alcohol | 10.0 g |

| | | |
|---|---|---|
| C₁₂–C₁₄ fatty alcohol + 2 EO-sulfate, Na salt (Texapon ® NSO), 28% solution | 25.0 | g |
| water | 15.0 | g |
| 2,5-diaminotoluene sulfate (p-toluylenediamine sulfate) | 7.5 | mmol |
| Coupler A 1 (or A 2 or V 4) | 7.5 | mmol |
| Na₂SO₃ | 1.0 | g |
| (NH₄)₂ SO₄ | 1.0 | g |
| ammonia solution (concentrated) | to pH = | 9.5 |
| water | to 100 | g |

EO = ethylene oxide

The components of the creme dye were mixed in the order given. After adding the developer and coupler compounds, first the pH value of the emulsion was adjusted to 9.5 with concentrated ammonia solution, then the mixture was made up with water to 100 g.

The oxidative development of the color was carried out with 3% hydrogen peroxide solution as an oxidizing agent. For this purpose 50 g of the hydrogen peroxide solution (3%) was added to 100 g of the emulsion and mixed. The creme dyes with oxidizer were promptly applied to standardized 90% grey strands of human hair about 5 cm long, not pretreated in any particular manner, and left thereon for 30 minutes at 27° C. After the end of the dyeing process the hair was rinsed with water, washed with a conventional shampoo, and dried.

The dyed hair strands were tested as follows for color intensity, fastness to cold permanent waving, fastness to friction and fastness to perspiration:

APPLICATIONS TESTING

1. Evaluation of the Color Intensity

The color intensity was evaluated immediately after the final coloring of the strands and rated according to the scale of five graded color intensitites.
Rating scale:
1=poor
2=moderate
3=satisfactory
4=good
5=very good.
The evaluations are reported in Table III

2. Testing of the Fastness to Cold Permanent Waving

A dyed, dried hair strand was saturated with a commercial cold permanent waving emulsion and held for 20 minutes at 27° C. Then the strand was rinsed well with water and treated for 10 minutes at 27° C. with a commercial permanent wave fixing solution, rinsed and dried.

The waving emulsion used was: Poly-Lock home permanent wave (waving emulsion).

The fixing solution used was: Poly-Lock home permanent wave (fixing).

The evaluation of the decolorization was performed according to the following rating scale:
1=shade altered
2=strands decolorized
3=marked weakening of the shade
4=slight weakening of the dhade
5=shade unchanged
The evaluations are reported in Table III.

3. Testing of Fastness to Friction

The fastness to friction was determined in analogy to DIN 54,021 (February 1971) using a universal friction testing device according to RUF (DIN 54,021, Section 7.2). The principle of this testing is described as follows:

A box sliding on rails is provided with a rubber membrane, onto which a piece of wool fabric according to DIN 54,000, 4.2×10.2 cm in size is placed. A cover provided with two windows is slid under the pin, closed and tightened in place with the screw. Then the two-windowed upper cover is hung in the hinge and the hair strands to be tested are uniformly distributed therein. An additional piece of fabric is placed on this so that no excessive strain is imposed on the upper rubber membrane. Then the upper box is closed and clamped with two screws.

A few blasts with the air pump bulge the membrane and with it, the test piece and the wool fabric with respect to one another, wherein the pressure is monitored on the manometer (0.3 kp/cm²). Pressure on the contact sets the box into back and forth movement. The counter records the strokes. After 50 (sliding) movements the test is interrupted, the compressed air allowed to escape through the valve, the test piece and the wool fabric removed from the apparatus, and the abrasion noted on the latter according to DIN 54,002. In this evaluation of the abrasion the fastness rating 5 indicates a very high fastness to friction, and rating 1 a low fastness to friction.

The evaluations are reported in Table III.

4. Testing of Perspiration Fastness

A dyed, dried hair strand was placed in a closable vessel in 25 ml of a synthetic perspiration fluid, and the vessel closed and stored for 7 hours at +50° C. The synthetic perspiration fluid was prepared according to COSMETICS & TOILETRIES, Vol. 94 (April 1979), p. 47 as follows:

| | |
|---|---|
| NaCl (sodium chloride) | 10.00 g |
| Na₂HPO₄ | 1.00 g |
| histidine hydrochloride | 0.25 g |
| water | to 1000.00 ml |
| lactic acid | to pH = 3.2 |

After storage the test strand was removed from the solution, rinsed with water and dried. The hair strand stored in the synthetic perspiration fluid was compared with an untreated strand and evaluated according to the following scale:
1=shade altered
2=strands decolorized
3=marked weakening of the shade
4=slight weakening of the shade
5=shade unchanged.
The result of the applications technology tests can be taken from the following Table III.

TABLE III

| Coupler | Shade nuance Color intensity | Cold wave fastness Shade nuance | Friction fastness | Perspiration fastness Shade nuance |
|---|---|---|---|---|
| A 1 Formula I, R = —CH₃ | blue-black 5 | 4–5 blue-black | 3 | 4–5 blue-black |

TABLE III-continued

| Coupler | Shade nuance Color intensity | Cold wave fastness Shade nuance | Friction fastness | Perspiration fastness Shade nuance |
|---|---|---|---|---|
| A 2 Formula I, R = —CH$_2$—CH$_2$—OH | blue-black 5 | 4–5 blue-black | 2–3 | 4–5 blue-black |
| V 4 Formula I, R = H | blue-black 5 | 3–4 black-brown | 1–2 | 4 black-brown |

These results demonstrate the high degree of resistance of the hair dyed with the oxidation hair dyestuff composition of the invention as compared with the dyestuff composition employing 2,3-diamino-6-metoxypyridine employed by Lange, U.S. Pat. No. 3,200,040.

The hair colorings obtained using the coupler 2,3-diamino-6-methoxypyridine (V 4) showed a marked change in shade under the influence of cold waving liquid (basis: ammonium thioglycolate) and perspiration. The frictional fastness of this hair coloring is also markedly lower.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. An oxidation hair dyestuff composition for the dyeing of human hair, comprising
    (a) from about 0.2 to 5 percent by weight of the combination of (1) at least one 2,3-diamino-6-methoxypyridine of the formula

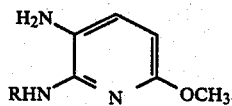

(I)

wherein R is methyl or hydroxyethyl, with (2) at least one compound selected from the group consisting of 0-phenylene diamine, p-phenylene diamine, 2-aminophenol, and 4-aminophenol, which may be unsubstituted or substituted by one or two $C_1$–$C_4$-alkyl or $C_2$–$C_4$-hydroxyalkyl on the nitrogen atom as well as by one or more $C_1$–$C_4$-alkyl, alkoxy having from 1 to 4 carbon atoms, or halogens on the aromatic nucleus, the molar ratio of component (1) to component (2) being from about 2:1 to 1:2,
    (b) from about 0.5 to 30 percent by weight of wetting and emulsifying agents,
    (c) from about 0.1 to 25 percent by weight of thickeners, and
    (d) the balance water.

2. The composition of claim 1, wherein the composition comprises from about 1 to 3 percent by weight of the combination of component (1) and component (2).

3. The composition of claim 1, wherein component (2) in said combination is selected from the group consisting of p-phenylene diamine, p-tolylene diamine and 2,5-diaminoanisole.

4. The composition of claim 1, wherein component (2) in said combination is p-tolylene diamine.

5. The composition of claim 1 wherein said molar ratio of component (1) to component (2) is within 10% of being equimolar.

6. The composition of claim 1 wherein said molar ratio of component (1) to component (2) is approximately equimolar.

7. A process for the dyeing of human hair comprising applying to said hair, at temperatures ranging substantially from about 15° to 40° C. for a time sufficient to effect dyeing through oxidation, an effective amount of the composition of claim 1 in an aqueous medium.

8. The process of claim 7, wherein the oxidation is effected by the action of a chemical oxidation agent.

* * * * *